(12) United States Patent
Marshall et al.

(10) Patent No.: US 8,797,021 B2
(45) Date of Patent: Aug. 5, 2014

(54) ELECTROCHEMICAL CORROSION POTENTIAL PROBE ASSEMBLY

(75) Inventors: Theron D. Marshall, Wilmington, NC (US); Adrian M. Mistreanu, Wilmington, NC (US); Angelito Foz Gonzaga, San Jose, CA (US); John S. Bennion, Hampstead, NC (US)

(73) Assignee: GE-Hitachi Nuclear Energy Americas LLC, Wilmington, NC (US)

( * ) Notice: Subject to any disclaimer, the term of this patent is extended or adjusted under 35 U.S.C. 154(b) by 566 days.

(21) Appl. No.: 13/026,969

(22) Filed: Feb. 14, 2011

(65) Prior Publication Data
US 2012/0206128 A1    Aug. 16, 2012

(51) Int. Cl.
*G01R 1/06* (2006.01)
(52) U.S. Cl.
USPC .......................................... 324/149
(58) Field of Classification Search
USPC .......................................... 324/149
See application file for complete search history.

(56) References Cited

U.S. PATENT DOCUMENTS

| | | |
|---|---|---|
| 5,375,151 A | 12/1994 | Gluntz et al. |
| 5,390,221 A | 2/1995 | Dix et al. |
| 5,465,278 A | 11/1995 | Cowan, II et al. |
| 6,391,173 B1 | 5/2002 | Kim et al. |
| 6,411,667 B2 | 6/2002 | Kim et al. |
| 7,060,177 B2 | 6/2006 | Law et al. |
| 2012/0155595 A1* | 6/2012 | Cabrera et al. ................ 376/245 |

FOREIGN PATENT DOCUMENTS

| | | |
|---|---|---|
| JP | 2006-201885 A | 8/2006 |
| JP | 2008-510997 A | 4/2008 |
| JP | 2010-060377 A | 3/2010 |

OTHER PUBLICATIONS

Wada et al., "Effects of Bulk Water Chemistry on ECE Distribution Inside a Crevice", 12th Intl Conf—Eviron Degration of Material in Nuclear Power System—Water Reactors (2005).
Uchida et al., "Water Chemistry Data Acquisition, Processing, Evaluation and Diagnosis Systems for Nuclear Power Reactors", 14th Intl Conf—Properties of Water and Steam in Kyoto.
The translated Office Action issued in connection with corresponding JP Patent Application No. 2012-028164 dated on Aug. 8, 2013.

* cited by examiner

Primary Examiner — Bot Ledynh
(74) Attorney, Agent, or Firm — Parks IP Law LLC; Stephen Terrell

(57) ABSTRACT

An electrochemical corrosion potential (ECP) probe assembly for monitoring ECP in a high velocity reactor line includes an airfoil shaped ECP cover that improves the streamlines over and around an ECP sensor. The airfoil shaped cover includes flow holes drilled normal to the surface of the ECP cover. As such, the direction of flow of reactor water into the ECP probe assembly is altered to reduce the flow rate internal to the ECP cover sufficiently to prevent damage to the ECP probes. To facilitate use as a retrofit component, the ECP cover may have an elliptical section that is contiguous to a circular section that conforms to the geometry of existing probe wells and probe sub-assemblies.

17 Claims, 6 Drawing Sheets

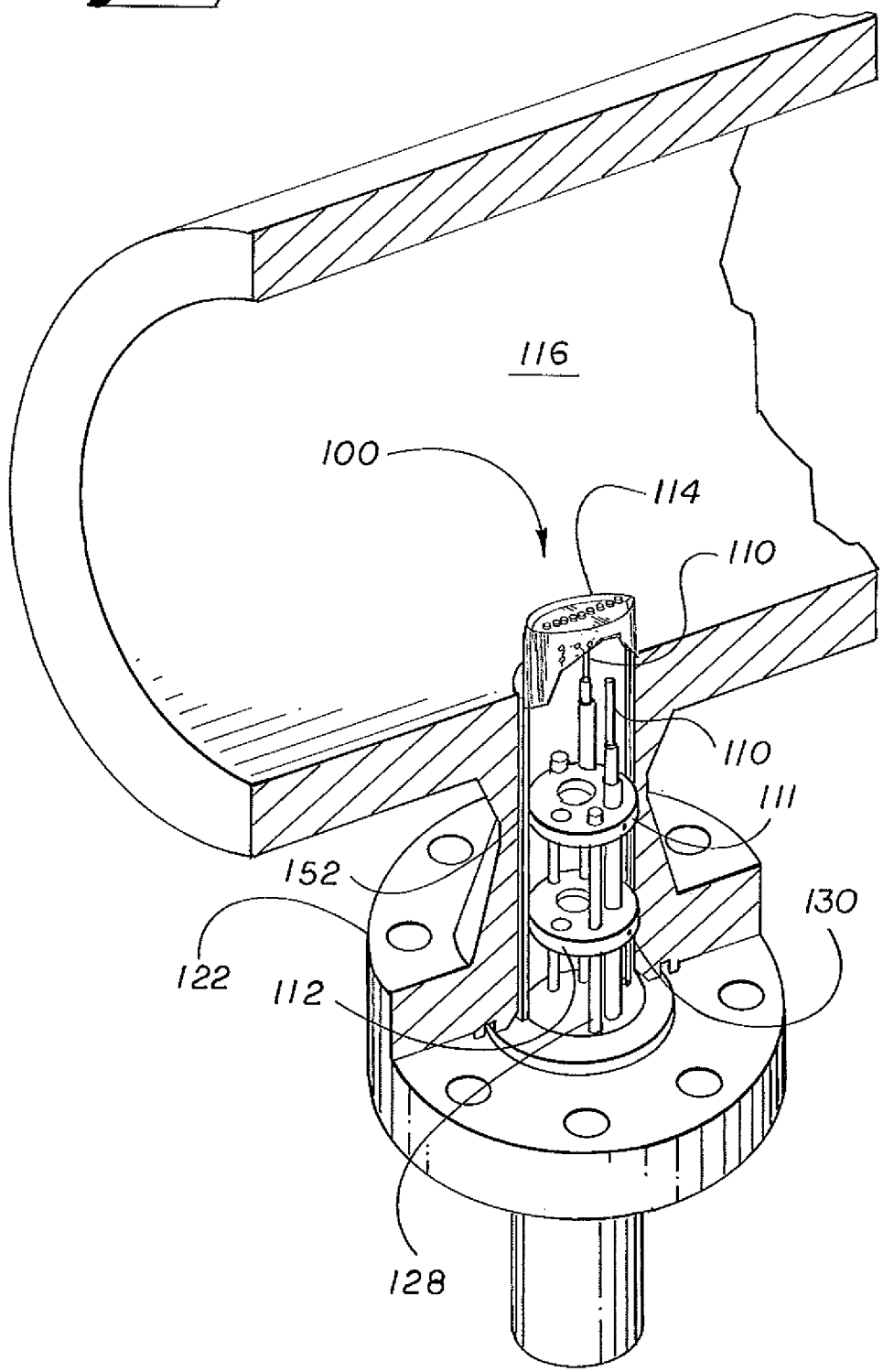
Fig_2

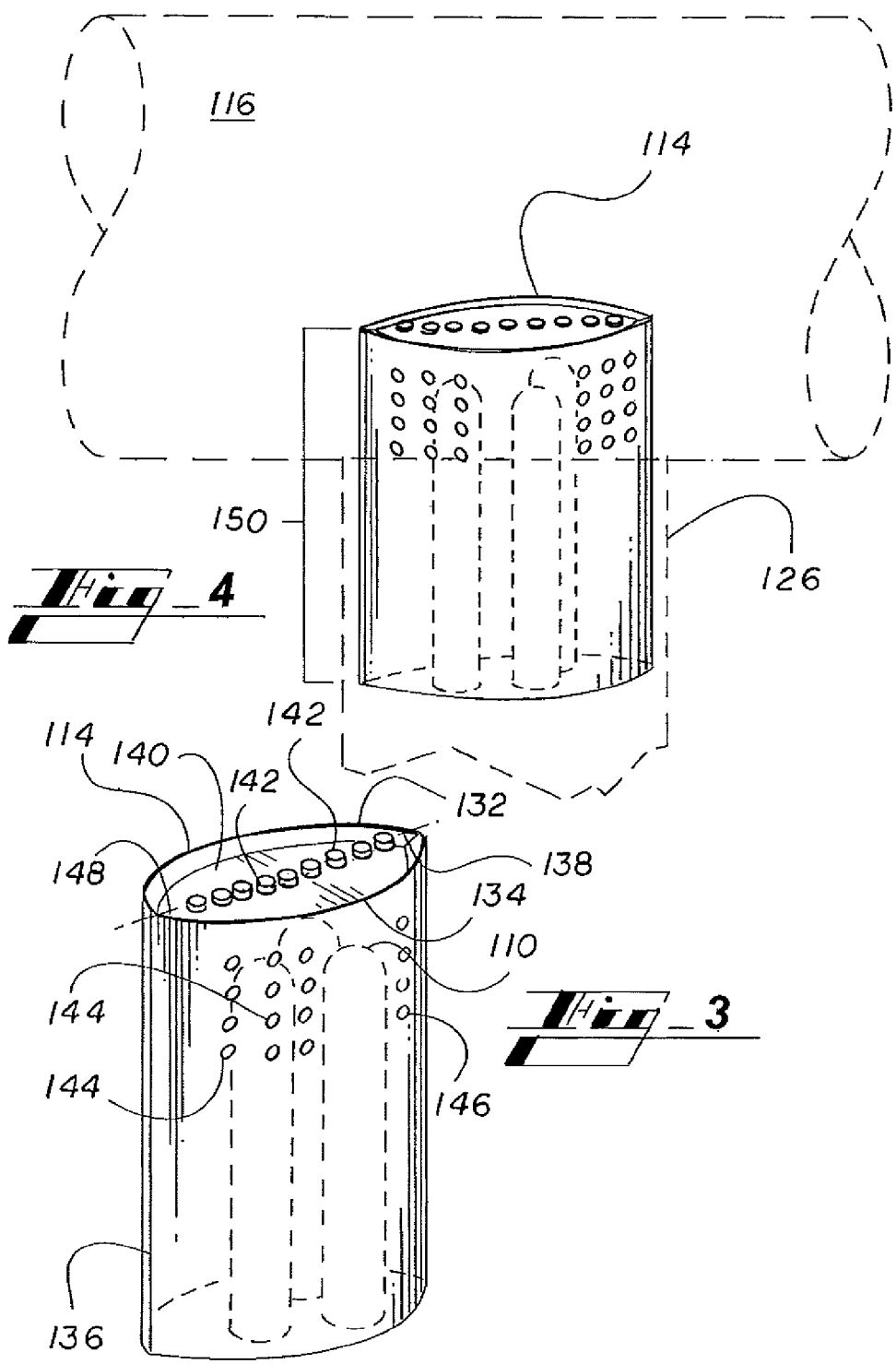

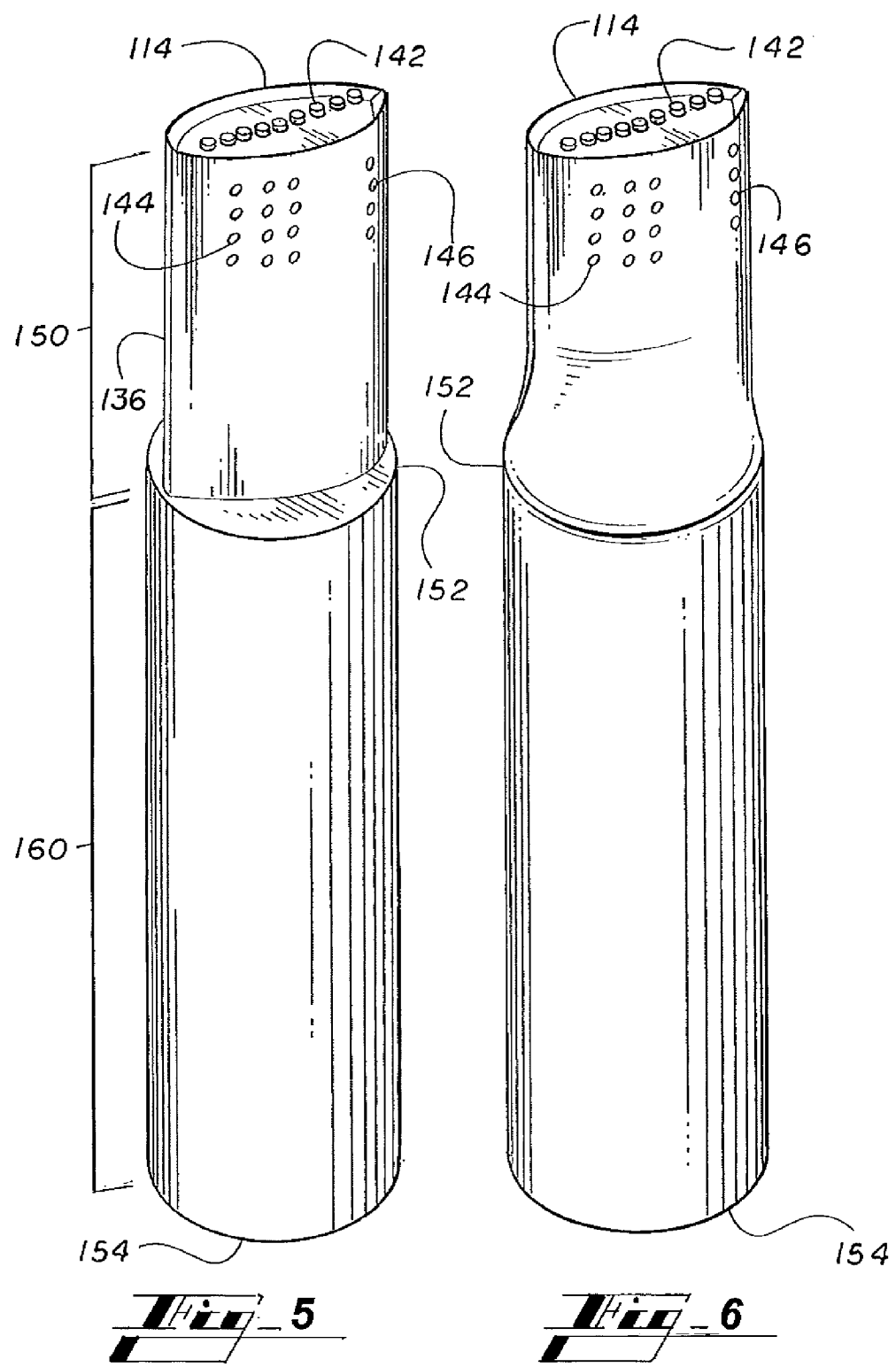

ELECTROCHEMICAL CORROSION POTENTIAL PROBE ASSEMBLY

TECHNICAL FIELD

The present invention relates generally to nuclear reactors, and more particularly, to an electrochemical corrosion potential probe assembly for monitoring water chemistry within a nuclear reactor system.

BACKGROUND OF THE INVENTION

It is known that monitoring water chemistry is essential to reliable, safe, and efficient operation of a reactor system. In particular, operators routinely collect data, on- and off-line, regarding the corrosive conditions caused in large part by the high operating temperature of and contaminants in the primary reactor water coolant.

In the context of a boiling water reactor (BWR), a Reactor Water Cleanup (RWCU) system maintains high reactor water quality by removing fission products, corrosion products, and other soluble and insoluble impurities. To remove undesirable chemical species and radioactive materials resulting from neutron activation of impurities and dissolved reactor materials, the RWCU may utilize a variety of means such as filtration and mitigation of corrosion. Generally, the water passes through isolation valves for redirection, heat exchangers for cooling, ion exchangers for undesired species removal, and the cleaned water is recirculated back into the reactor core.

Ideally, corrosion mitigation is performed precisely, selectively and locally, often by injecting hydrogen into reactor feed water. Hydrogen water chemistry (HWC) dilutes and counteracts oxidizing species, such as oxygen and hydrogen peroxide. Otherwise, these species may contribute to intergranular stress corrosion cracking (IGSCC) of susceptible materials, such as stainless steel reactor components.

Precise and selective mitigation is desirable because the level of mitigation that is appropriate for one reactor may be unwarranted for another, and the cost and negative impact of unnecessary measures are detrimental. For example, excessive HWC can generate unacceptable high radiation levels and doses.

Local mitigation is often desirable because flow rates and radiation levels vary at different locations within the reactor system, which impacts the amount of hydrogen necessary to achieve oxygen concentrations that will reduce the electrochemical corrosion potential (ECP) of materials within the reactor.

ECP sensors are commonly distributed to continuously monitor water chemistry at various sample sites throughout the reactor system, so that mitigation is tailored to actual conditions present in the system and to predict performance of specific reactor components. To measure oxygen concentration, for example, an ECP sensor is configured and positioned to function "in-line" with the flow at the sample site, such that reactor water flows into the sensor and around one or more ECP probes. ECP sensors are often placed in welding neck flanges in primary system piping (e.g., reactor recirculation lines, bottom head drain lines, and reactor cleanup lines). As used herein, the term "ECP sensor" refers to an ECP probe assembly that includes one or more ECP probes, and that may further include additional associated components, such as but not limited to, cables or wires, connectors, fittings, and encasements.

The typical BWR ECP sensor operates in a harsh environment—high-levels of radiation exposure, water flow rates of several meters per second, and water temperatures as high as 300° C. The primary threat to the ECP sensor is excessive turbulence at or flow rates around the sensor probes during RWCU operation. High water flow rates around the ECP probe may damage the probe and introduce debris from the probe into the reactor water recirculation loop. This debris is of particular concern because it has the potential to damage pump vanes, clog filter screen, or in the worst case scenario, become lodged in the fuel rod spacers and cause fretting of the fuel rod cladding. A secondary consequence of a damaged ECP sensor is that ECP measurements will be inaccurate or impossible, so sensor failure can yield a useful life that is far less than a single fuel cycle. Lastly, the geometry and orientation of the ECP probes may induce or increase vortex shedding and flow induced vibration in the RWCU pipes. Therefore, there is a need for systems and methods for preventing ECP sensor damage during reactor operation.

BRIEF DESCRIPTION OF THE INVENTION

The present invention addresses the problem of detrimental turbulence and flow rates with an ECP sensor that includes an ECP cover having a geometry that improves flow streamlines, and reduces internal flow through the ECP sensor without creating a high pressure differential that will stress the ECP probes or cover component. The ECP cover thereby reduces the potential for probe damage, which decreases the possibility of probe debris contaminating the reactor water loop and increases the ECP sensor reliability.

Prior to this invention, an engineering effort was made to create a "parts catcher cover" for the ECP sensor. This proposed cover addressed the consequence of the problem of high flow rate around the ECP probe problem, that is, the cover is intended to catch ECP probe debris and keep it from entering the reactor water flow loop. Instead of addressing the consequence of the problem, this invention addresses the source of the problem and eliminates the high water flow rate around the ECP probes. The ECP cover achieves its goal via improved geometry and configuration of the flow holes in the ECP cover. Advantageously, the principles and teachings of the various embodiments significantly increase the service life of ECP probes and other ECP sensor components, reduce the need for replacement or compensation for damaged metal reactor parts and fuel cladding, and decrease service and maintenance requirements for the ECP probes.

According to a first aspect, an ECP probe assembly includes an ECP cover that has a geometry that yields marked improvements in performance of an ECP sensor without substantially negatively impacting flow dynamics within a conduit. Specifically, in certain embodiments the cross-section of at least the distal portion of the ECP cover has an airfoil shape, that is, a shape that can be described as elliptical with a pointed leading and trailing edge, which might be referred to commonly as an elongated football shape. This shape beneficially reduces drag and undesirable effects (e.g., vortex shedding) within a conduit through which reactor water flows. As used here, the term "conduit" refers to a channel through which a fluid is conveyed, including but not limited to a pipe, tube, raceway, cavity, opening, shaft, portal, and the like. In certain embodiments, the ECP cover is configured to be usable in an existing probe well that is a substantially circular cylinder in shape, and with existing probe sub-assemblies. To that end, only the distal end of the ECP cover, that is, the end that extends into the conduit, is elliptical in shape, while the lower section is circular in shape to conform to the probe well. In certain of these embodiments, the elliptical section of the ECP cover transitions to the circular section abruptly, while in others of these embodiments, the transition is a gradual change in cross-sectional shape. The two different sections may be fabricated separately and joined in either case, as dictated by manufacturing considerations.

In certain embodiments, the ECP cover can be fabricated from two substantially identical planar side panels of sheet metal or other suitable material, which are joined together to define a leading edge seam and a trailing edge seam. The leading and trailing edges are brought toward one another to bow the side panels and define the airfoil shape, that is, the elliptical cross-section with pointed edges defined by the seams. Those skilled in the art will appreciate that, without departing from the spirit of the invention, an airfoil-shaped cylinder can be formed in a number of alternative ways, such as but not limited to by extrusion, or from a single side panel that is joined at opposed edges to form one of the leading and trailing edges and creased at the center to form the other of the leading and trailing edges. A top panel encloses one open end of the ECP cover, creating a partially closed airfoil shaped (elliptical) cylinder.

According to a second aspect, the ECP cover has flow holes drilled through the cover to allow fluid contact with the ECP probes at significantly lower flow rates. The number and positions of the flow holes are preferably optimized to yield the desired result without unnecessary increases in complexity or cost of manufacturing. Without this optimization, ECP covers may expose the ECP probes to relatively high flow velocities that yield hydraulic loads that fracture ECP probes, thereby hampering water chemistry measurement and control, and potentially introducing metal pieces into the reactor water flow loop to become irradiated, impact pump impellers, or more critically, cause fuel cladding failure via fretting.

More specifically, in a first embodiment, the flow holes of an ECP cover are drilled normal to the surface of cover. Consequently, at least some of the flow holes of this embodiment are not drilled in the direction of flow through the conduit. Thus, the water entering the ECP cover to flow across the ECP probes has to change flow direction to flow into the flow holes, which causes an energy loss that provides a decrease in the internal flow rate. As an added benefit, drilling the flow holes normal to the surface of the ECP cover simplifies manufacturing. As mentioned above, the sides of the ECP cover can be formed from two panels, so prior to joining the two panels, the flow holes can be drilled through each panel while it is in a flattened condition.

In these embodiments, desired results can be achieved with the following arrangement of flow holes, although it should be noted that other configurations may be successful as well. A single row of flow holes is formed in the top panel and in alignment with an imaginary chord extending between the pointed ends of the airfoil shaped ECP cover. A cluster of flow holes is formed adjacent to and on both sides of the leading edge seam for ingress, and another cluster of flow holes is formed adjacent to and on both sides of the trailing edge seam for egress. For example, the top panel may bear nine flow holes aligned with the chord, and each cluster of flow holes formed in the side panels can include twelve flow holes arranged in four rows of three.

In an alternative embodiment, the flow holes are drilled parallel to the direction of flow through the conduit.

The various embodiments of ECP covers can be implemented as part of an ECP probe assembly that includes several ECP probes. In certain of these embodiments, three probes (for example, two platinum probes and one iron probe) are enveloped by a single one of the various ECP cover embodiments.

As will be described in more detail below, the various aspects of the invention considerably reduce flow to prevent excessive hydrodynamic loading of the ECP probe, while allowing sufficient flow to enable dynamic corrosion monitoring. Applications for the various embodiments include monitoring makeup water, condensate water, feed water, steam, cooling tower water, blow down, and effluent water.

The foregoing has broadly outlined some of the aspects and features of the various embodiments, which should be construed to be merely illustrative of various potential applications. Other beneficial results can be obtained by applying the disclosed information in a different manner or by combining various aspects of the disclosed embodiments. Other aspects and a more comprehensive understanding may be obtained by referring to the detailed description of the exemplary embodiments taken in conjunction with the accompanying drawings, in addition to the scope defined by the claims.

BRIEF DESCRIPTION OF DRAWINGS

FIG. 2 is a cross-sectional partial perspective view showing one embodiment of an ECP probe assembly of the present invention, including exemplary ECP sensors and a novel ECP cover, the monitoring system being configured to monitor water chemistry in an exemplary conduit.

FIG. 3 is a perspective view of the elliptical section of the ECP probe assembly of FIG. 2.

FIG. 4 is a partial perspective view of the elliptical section of the ECP probe assembly of FIG. 2, as positioned within a portion of an exemplary conduit and probe well.

FIGS. 5 and 6 are perspective views of a first and a second embodiment of the ECP cover, showing an abrupt and a gradual transition between the elliptical section and the circular section of the ECP cover.

DETAILED DESCRIPTION OF THE INVENTION

As required, detailed embodiments are disclosed herein. It must be understood that the disclosed embodiments are merely exemplary of and may be embodied in various and alternative forms, and combinations thereof. As used herein, the word "exemplary" is used expansively to refer to embodiments that serve as illustrations, specimens, models, or patterns. The figures are not necessarily to scale and some features may be exaggerated or minimized to show details of particular components. In other instances, well-known components, systems, materials, or methods that are known to those having ordinary skill in the art have not been described in detail in order to avoid obscuring the present disclosure. Therefore, specific structural and functional details disclosed herein are not to be interpreted as limiting, but merely as a basis for the claims and as a representative basis for teaching one skilled in the art.

Figure 1:
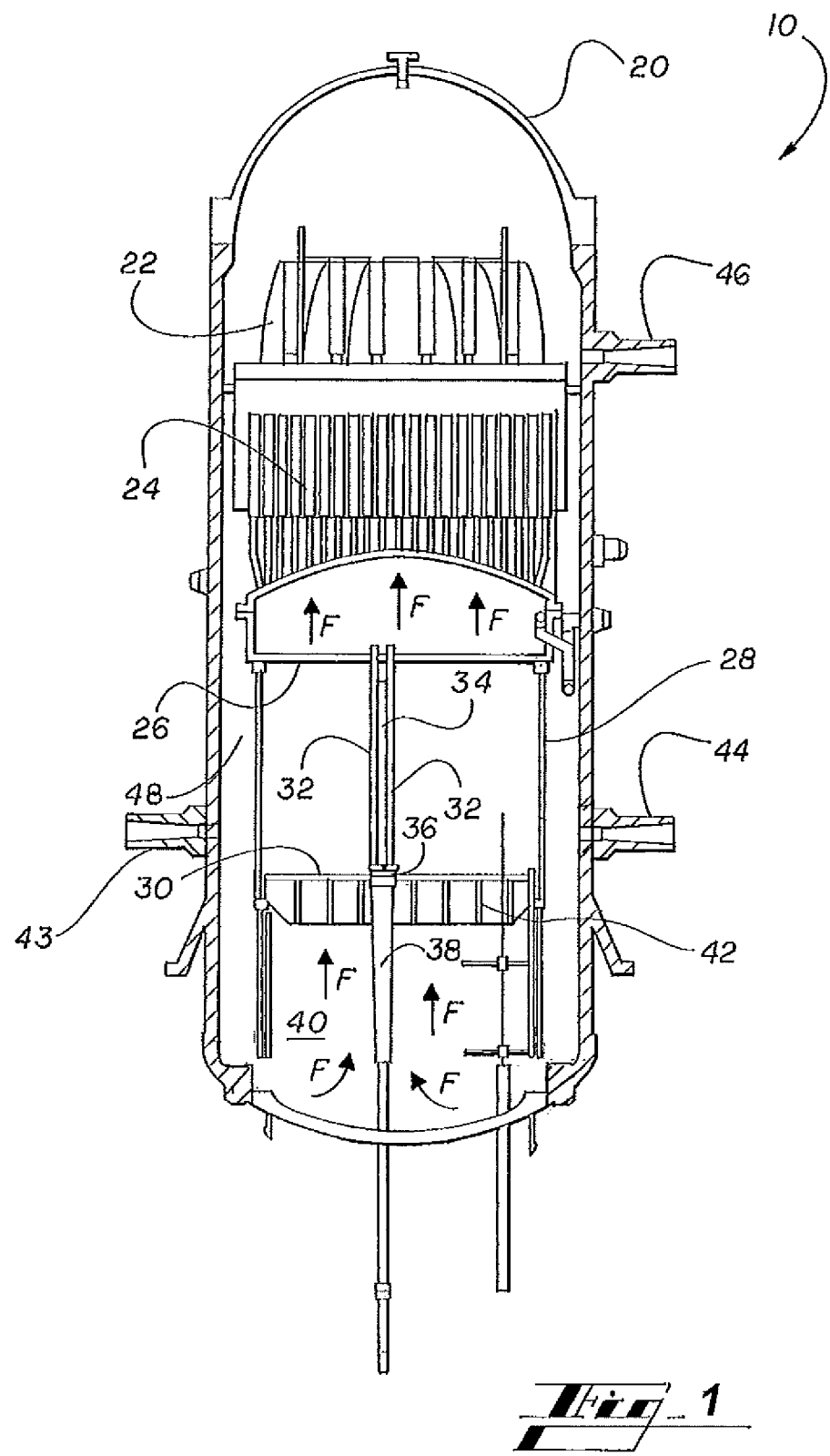
FIG. 1 is a schematic cross-sectional view illustrating the structure of an exemplary reactor pressure vessel of a boiling water reactor in accordance with an exemplary environment of the invention.

An exemplary environment for implementing the various embodiments of the present invention is a boiling water reactor (BWR). Referring to FIG. 1, the general structure of a BWR 10 is illustrated, although those skilled in the art will readily appreciate that every power plant is substantially unique. The BWR 10 includes a reactor pressure vessel 20, a steam dryer 22, a steam separator 24, a top guide 26, a core shroud 28, a core support plate 30, fuel assemblies 32, control rods 34, fuel support members 36, control rod guide tubes 38, a lower plenum 40, reinforcing beams 42, recirculation water inlet 43, recirculation water outlet 44, and main steam lines 46.

Pressure is generated in the lower plenum 40 by the external recirculation pumps (not shown) such that coolant (e.g., water) flows from the lower plenum 40 through the fuel support members 36 into the fuel assemblies 32. In the fuel assemblies 32, the coolant is heated to produce a two-phase flow including vapor and liquid components. The vapor and liquid components are separated by reactor systems including steam separators 24 and the steam dryer 22. For example, liquid is separated from vapor by the steam separator 24, with the liquid returned to an annulus (downcomer) 48 and then to external recirculation pumps (not shown), and the vapor (with a small amount of residual liquid) directed into the steam dryer 22. The remaining liquid is separated from the vapor by the steam dryer 22, again with the liquid returned to the downcomer 48, and the vapor directed into a turbine 50 (FIG. 8) through main steam lines 46.

Referring to FIGS. 1 and 2, an ECP probe assembly 100 includes electrochemical potential (ECP) probes 110, an upper brace 111 and a lower brace 112 for lateral support of the ECP probes 110, and an ECP cover 114. The ECP probes 110 transmit signals that are analyzed by a suitable processor (not shown) in an analysis instrument for collecting and processing data sensed by the ECP probes 110.

Figure 7:
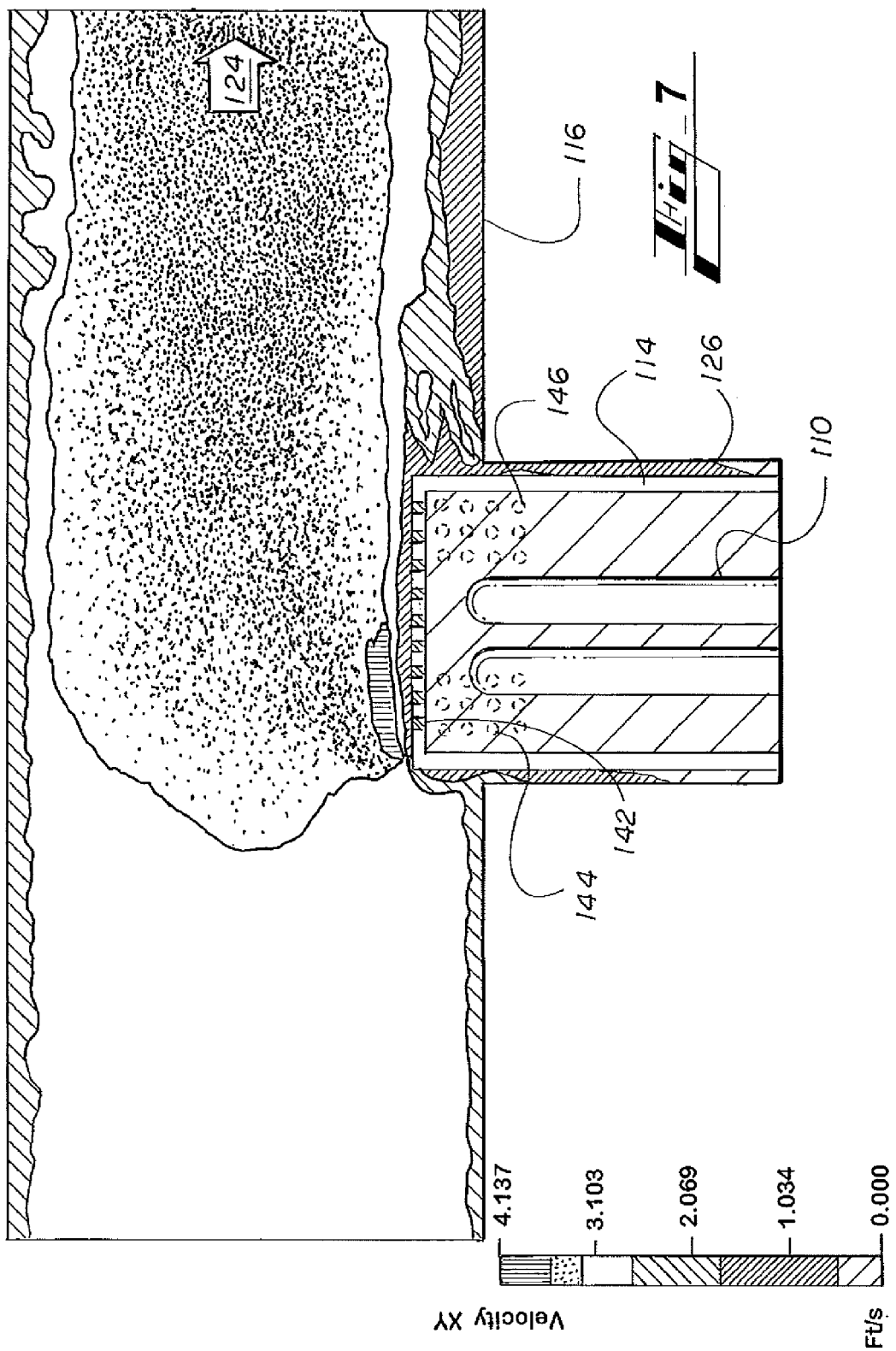
FIG. 7 is a graphical cross-sectional elevational illustration of the ECP probe assembly of FIG. 2, illustrating flow velocities of fluid traveling through the ECP cover and across the ECP probes.
Figure 8:
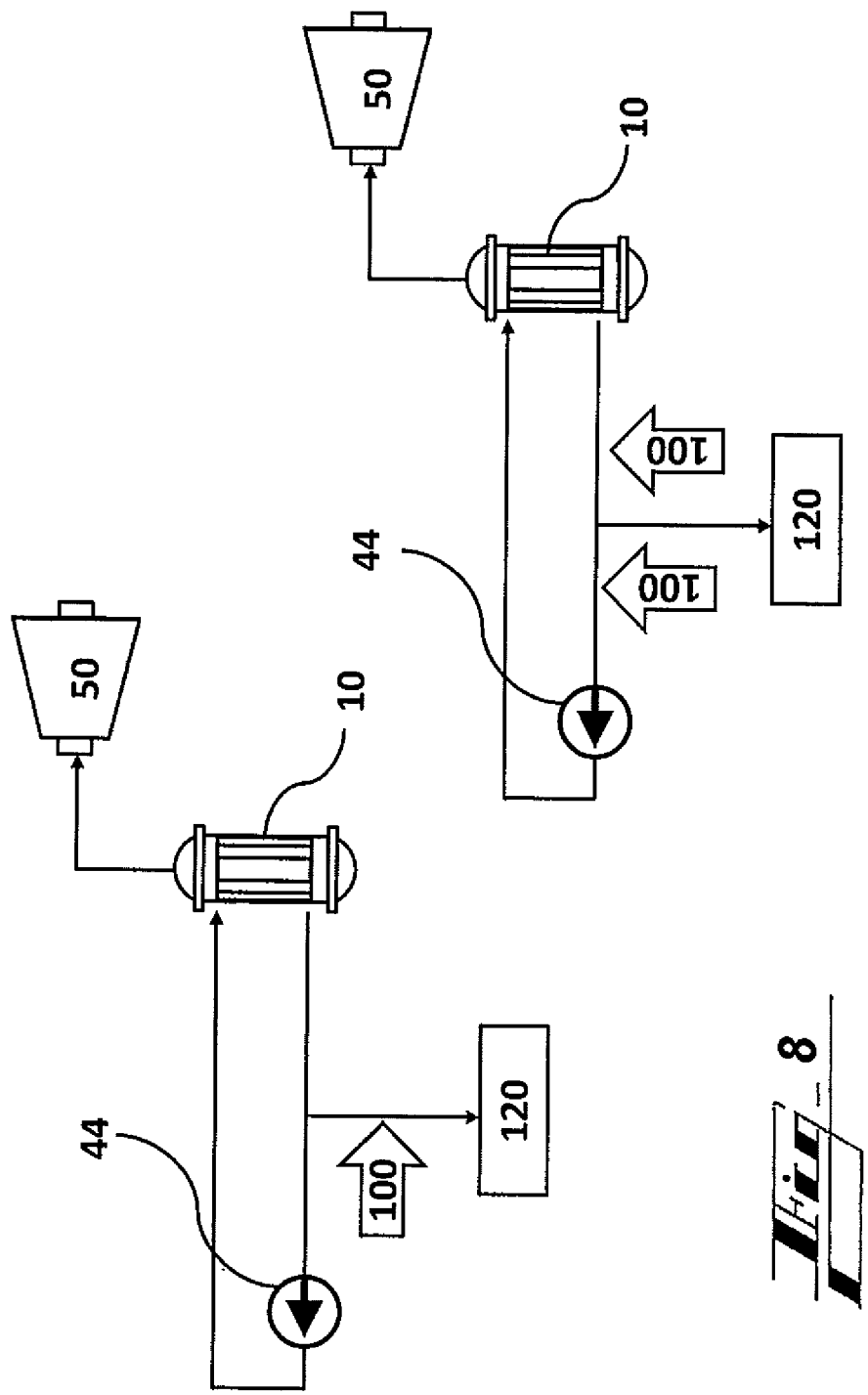
FIG. 8 is a schematic of a BWR system, showing examples of various potential sampling sites at which the ECP probe assembly can be installed.

The illustrated ECP probe assembly 100 is configured to measure the ECP of water in a conduit 116 that is upstream or downstream from a reactor water cleanup (RWCU) system 120 (shown in FIG. 8). Particularly, the exemplary ECP probe assembly 100 is mounted in a flange 122 (shown in FIG. 2) attached to the conduit 116 such that the ECP probes 110 and ECP cover 114 partially extend into or otherwise encounter the flow 124 (FIG. 7) through a conduit 116. In FIG. 2, the flange assembly is shown in its upside-down orientation although the ECP probe assembly can be mounted in any azimuthal orientation relative to the pipe axis.

The ECP probe assembly 100 is configured to monitor various fluid properties in various parts of the BWR 10 such as reactor recirculation lines, bottom head drain lines, reactor clean up lines, other flange locations, and the like.

For purposes of teaching, the ECP probes 110 are described as devices for detecting and signaling in response to the presence of electrochemical stimuli that are associated with electrochemical corrosion potential (ECP). Generally, ECP measurements are made to determine whether intergranular stress corrosion cracking (IGSCC) is likely to occur, to monitor water chemistry changes that lead to unacceptable crack growth rates, and the like. However, the principles and teachings can be employed with any known or yet to be developed electrochemical sensor and probe design.

The illustrated ECP probe assembly 100 includes three ECP probes 110: two that are primarily formed from platinum and one from iron. For example, iron/iron oxide ECP probes 110 are used for measurements without hydrogen injection and platinum ECP probes 110 are used for measurements during hydrogen injection. In alternative embodiments, ECP probes may be manufactured at least in part from other materials, such as stainless steel and carbon steel are used. It is also contemplated that ECP probe technology may vary and evolve, without impacting the applicability of the various embodiments taught in the present disclosure.

Referring now to FIGS. 2-4, the three ECP probes 110 are enveloped by the ECP cover 114, which protects the ECP probes 110 from high flow velocities and debris, and acts as a catch to prevent a broken ECP probe 110 from entering and damaging the systems of the BWR 10. The ECP probe assembly 100 extends into a probe well 126 and into the conduit 116. Each of the three ECP probes 110 receives lateral support and stabilization from the upper brace 111 and the lower brace 112, and the braces 111, 112 receive longitudinal support from posts 128. The ECP cover 114 is mounted and further stabilized by welding or otherwise connecting the ECP cover 114 to the braces 111, 112 at cover mounts 130.

At least the distal portion of the ECP cover 114 is an elliptical cylinder with pointed ends, i.e., an airfoil shaped component. As will be described in more detail below, the opposing end of the ECP cover 114 may taper or abruptly transition to a circular cylindrical shape, to conform to the shape and dimensions of an existing probe well 126. In any event, at least the distal end of the elliptical section of the ECP cover 114 extends at least partially into the conduit 116 such that it breaks the plane of the inside surface of the conduit 116 to encounter the flow 124 of reactor water therethrough.

An exemplary method for manufacturing the ECP cover 114 will now be described, with reference to FIG. 3. The ECP cover 114 shown is formed by aligning a first side panel 132 with a second side panel 134 to facilitate joining the vertical edges of the panels 132, 134 to define a leading edge seam 136 and a trailing edge seam 138. In this condition, the first side panel 132 with a second side panel 134 form a flattened tubular structure. The leading edge seam 136 and a trailing edge seam 138 are brought toward one another such that the first side panel 132 with a second side panel 134 bow apart from one another to define a cavity therebetween, and to define the afore-mentioned airfoil shape. A top panel 140 is applied to enclose one end of the ECP cover 114.

While protecting the ECP probes 110 from high flow velocities, the ECP cover 114 is configured to allow fluid traveling through the RWCU line 120 to flow over the ECP probes 110 such that the ECP probes 110 can measure properties of the fluid. The pattern and number of flow holes is selected to optimize performance. In the exemplary embodiment, the top panel 140 includes a single line of nine top flow holes 142, all aligned along an imaginary longitudinal chord line 148 that connects the leading and trailing edge seams of the airfoil shaped ECP cover 114. Each of the first side panel 132 and the second side panel 134 includes a cluster of leading flow holes 144 adjacent to the leading edge seam 136 and a cluster of trailing flow holes 146 adjacent to the trailing edge seam 138.

In the embodiment shown, the flow holes 142, 144, 146 are drilled in the first side panel 132, second side panel 134 and top panel 140 prior to assembly of the ECP cover 114. In this manner, the flow holes 142, 144, 146 easily can be drilled normal to the surface of the ECP cover 114.

Referring now to FIGS. 5 and 6, which are perspective views of two alternative embodiments of the ECP cover 114, the ECP cover 114 may be an elliptical cylinder altogether, but for retrofit applications may benefit from a combination shape. In other words (and with additional reference to FIG. 2), an existing probe well 126 that was used with a prior art ECP cover (not shown) is a circular cylinder. The upper brace 111 and lower brace 112 are circular as well. Accordingly, in such an environment, it is desirable to obtain the benefits of the elliptical geometry on flow dynamics, without altering the geometries of the probe well 126 and probe sub-assembly (braces 111/112 and probes 110). FIG. 5 illustrates an ECP cover 114 with an elliptical section 150 with an abrupt transition 152 to a circular section 160 that extends to the bottom edge 154 of the ECP cover 114. FIG. 6 illustrates an alternative ECP cover 114 with an elliptical section 150 with a more gradual transition 152 to the circular section 160 that extends to the bottom edge 154 of the ECP cover 114. In either embodiment, the elliptical section 150 can be formed separately from the circular section 160, and then the sections can be joined together to create an integral component. It is contemplated that, alternatively, the entire ECP cover 114 can be fabricated as a single unitary component. The transition 152 begins or occurs in the embodiment shown in FIG. 2 at the height of the upper brace 112.

Referring to FIG. 7, three-dimensional (3D) computational fluid dynamics (CFD) analyses of the exemplary embodiments of the present invention demonstrate that the ECP cover 114 limits flow over the ECP probes 110 to an average flow velocity between 0.3 and 0.05 f/ts, with average flow rates in the conduit 116 of approximately 1-4 ft/s. This is a substantial reduction when compared to other known configurations of covers, which often have circular cross sections that expose ECP probes to fluid velocities averaging 4 ft/s. Accordingly, the exemplary ECP cover 114 will extend the current service life due to the reduced hydraulic loading experienced by the ECP probes 110. In addition, the exemplary ECP cover 114 reduces drag and lift forces.

As stated above, power plants differ structurally in many ways, and further, the sample sites may vary widely in pressure, temperature and flow conditions. FIG. 8 is a schematic diagram that shows a few potential sampling sites for placement of ECP probe assemblies 100. Those skilled in the art will readily appreciate that ECP probe assemblies 100 may be installed in one location, several locations simultaneously, and in various sites to measure the ECP in the plant: e.g., near the core support plate 30, lower plenum 40, as well as in the lines associated with recirculation pumps 44.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An electrochemical corrosion potential (ECP) probe assembly, comprising:
   at least one ECP probe; and
   a probe cover enclosing the at least one ECP probe, comprising:
      an elliptical cylinder that extends around the at least one ECP probe, the cylinder having a leading edge seam and a trailing edge seam;
      a top panel that encloses an end of the elliptical cylinder; and
      a plurality of leading flow holes formed on both sides of the leading edge seam and a plurality of trailing flow holes formed on both sides of the trailing edge seam.

2. The ECP probe assembly of claim 1, wherein the leading flow holes and the trailing flow holes are drilled normal to the surface of the probe cover.

3. The ECP probe assembly of claim 1, further comprising top flow holes formed in the top panel.

4. The ECP probe assembly of claim 3, wherein the top flow holes are arranged in a single row extending longitudinally across the top panel.

5. The ECP probe assembly of claim 1, wherein the probe cover further comprises a circular cylinder that is connected to the elliptical cylinder at a transition.

6. The ECP probe assembly of claim 5, further comprising an upper brace that is configured to support the at least one ECP probe, the upper brace being enclosed by the circular cylinder of the probe cover.

7. An electrochemical corrosion potential (ECP) cover for an ECP probe assembly, comprising:
   a first side panel;
   a second side panel hingedly connected to the first side panel along opposed side edges to define a leading edge seam and a trailing edge seam; and
   wherein the first side panel and the second side panel are bowed away from one another to define an elliptical cylindrical section that is configured to enclose at least one ECP probe.

8. The ECP cover of claim 7, further comprising a top panel enclosing one end of the elliptical cylindrical section.

9. The ECP cover of claim 7, further comprising a cluster of leading flow holes formed adjacent to the leading edge seam and a cluster of trailing flow holes formed adjacent the trailing edge seam.

10. The ECP cover of claim 9, wherein the leading flow holes and the trailing flow holes are drilled normal to the surface of one of the first side panel and the second side panel.

11. The ECP cover of claim 9, wherein the cluster of leading flow holes and the cluster of trailing flow holes each comprise four rows of three.

12. The ECP cover of claim 9, wherein the cluster of leading flow holes is spaced apart from the cluster of trailing flow holes.

13. The ECP cover of claim 8, further comprising a row of flow holes formed in the top panel.

14. The ECP cover of claim 13, wherein the row of flow holes extends longitudinally across the top panel.

15. An electrochemical corrosion potential (ECP) cover for an ECP probe assembly, comprising:
   a cylinder configured to extend around the ECP probe assembly; and
   a plurality of flow holes on a surface of the cylinder, wherein the flow holes are arranged on the surface of the cylinder at positions that are normal to a direction of coolant flow through the cylinder.

16. The ECP cover of claim 15, further comprising a top panel enclosing an end of the cylinder;
   wherein the top panel includes a further plurality of flow holes drilled through arranged on the top panel.

17. The ECP cover of claim 16, wherein the further plurality of flow holes are arranged on the surface of the top panel at positions that are parallel to a direction of coolant flow through the cylinder.

* * * * *